(12) United States Patent
Shiroishi et al.

(10) Patent No.: US 12,154,681 B2
(45) Date of Patent: Nov. 26, 2024

(54) MEDICAL IMAGE DIAGNOSIS APPARATUS, DISINFECTION MANAGEMENT APPARATUS AND DISINFECTION APPARATUS

(71) Applicant: CANON MEDICAL SYSTEMS CORPORATION, Otawara (JP)

(72) Inventors: Ryo Shiroishi, Nasushiobara (JP); Gakuto Aoyama, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 826 days.

(21) Appl. No.: 17/307,064

(22) Filed: May 4, 2021

(65) Prior Publication Data

US 2021/0350912 A1 Nov. 11, 2021

(30) Foreign Application Priority Data

May 11, 2020 (JP) ................................ 2020-083512

(51) Int. Cl.
| | | |
|---|---|---|
| G16H 40/20 | (2018.01) | |
| A61B 5/00 | (2006.01) | |
| A61B 6/03 | (2006.01) | |
| A61L 2/24 | (2006.01) | |
| G16H 10/60 | (2018.01) | |
| G16H 50/20 | (2018.01) | |

(52) U.S. Cl.
CPC ............ *G16H 40/20* (2018.01); *A61B 5/0077* (2013.01); *A61B 6/032* (2013.01); *A61L 2/24* (2013.01); *G16H 10/60* (2018.01); *G16H 50/20* (2018.01); *A61L 2202/14* (2013.01); *A61L 2202/25* (2013.01)

(58) Field of Classification Search
CPC ..... A61B 1/00142; A61B 1/121; A61B 1/122; A61B 1/126; A61B 1/127; A61B 1/128; G16H 40/40; A61L 2202/14
See application file for complete search history.

(56) References Cited

U.S. PATENT DOCUMENTS 11,278,637 B2 * 3/2022 Kupa ................... A61L 2/0047

FOREIGN PATENT DOCUMENTS

| JP | 2003-290191 A | 10/2003 |
|---|---|---|
| JP | 2005-198761 A | 7/2005 |

* cited by examiner

*Primary Examiner* — Don K Wong
(74) *Attorney, Agent, or Firm* — Oblon, McClelland, Maier & Neustadt, L.L.P.

(57) ABSTRACT

A medical image diagnosis apparatus according to an embodiment is installed in an examination room and includes an obtaining unit, a judging unit, and an output unit. The obtaining unit is configured to obtain patient information about a patient undergoing an image diagnosing process that uses the medical image diagnosis apparatus. The judging unit is configured to determine specifics of control related to disinfection, on the basis of the patient information. The output unit is configured to output the determined specifics of the control.

15 Claims, 3 Drawing Sheets

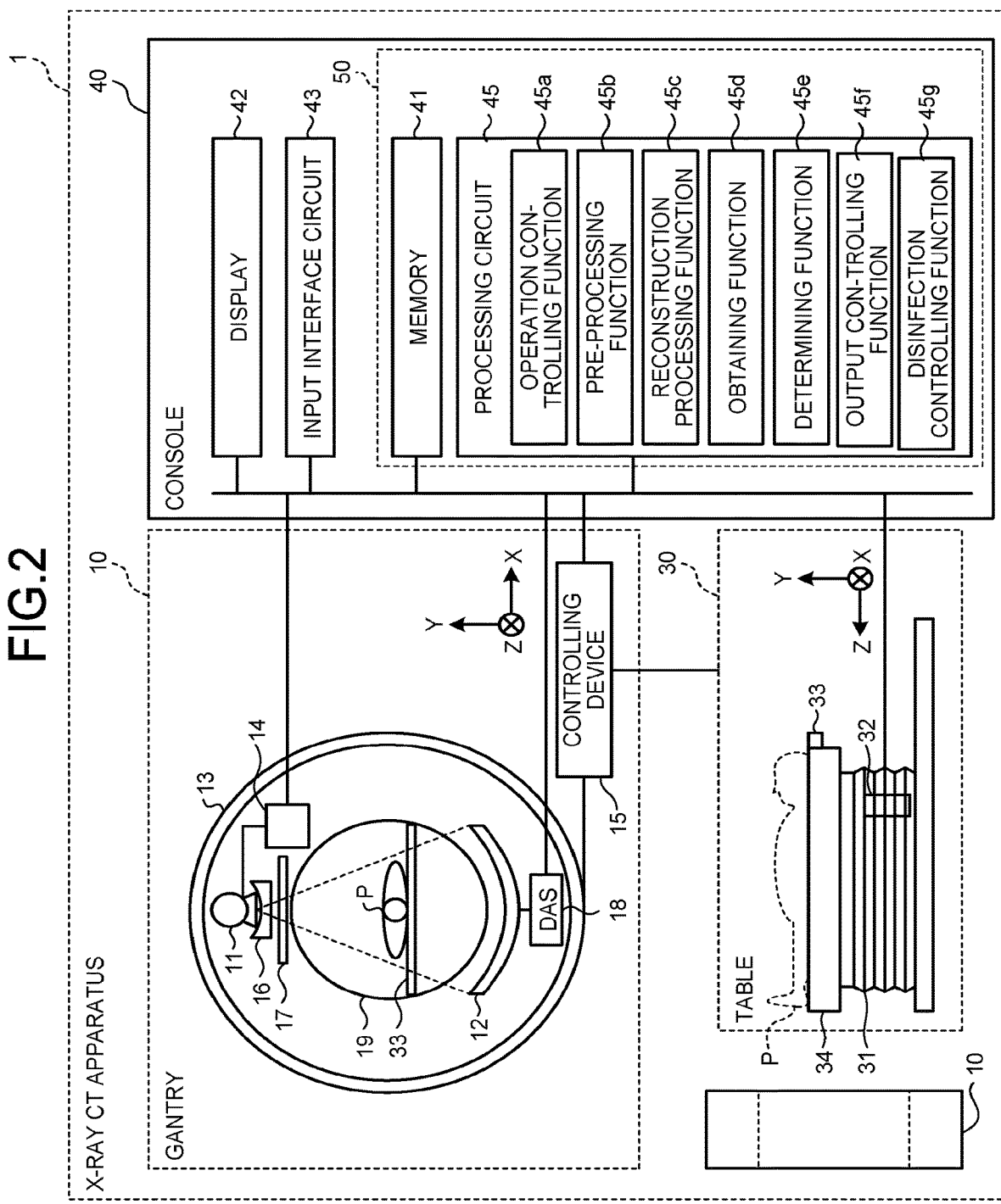

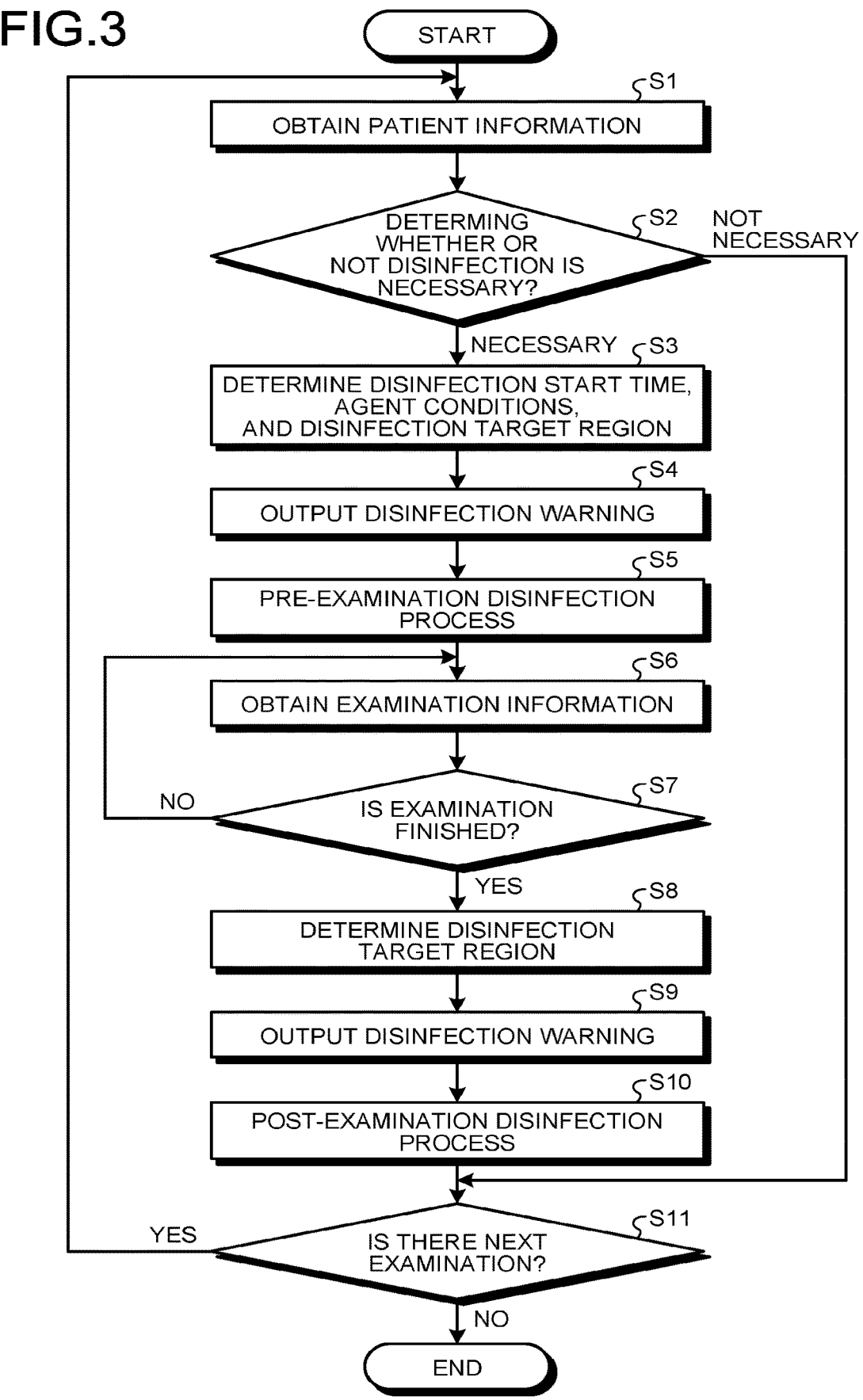

MEDICAL IMAGE DIAGNOSIS APPARATUS, DISINFECTION MANAGEMENT APPARATUS AND DISINFECTION APPARATUS

CROSS-REFERENCE TO RELATED APPLICATIONS

This application is based upon and claims the benefit of priority from Japanese Patent Application No. 2020-083512, filed on May 11, 2020; the entire contents of which are incorporated herein by reference.

FIELD

Embodiments described herein relate generally to a medical image diagnosis apparatus, a disinfection management apparatus and a disinfection apparatus.

BACKGROUND

For example, as an infectious disease preventive countermeasure, it is necessary to disinfect medical image diagnosis apparatuses or examination rooms in some situations. According to a conventional method, medical staff who carry out medical examinations (hereinafter, "examinations") such as medical doctors, technologists, or nurses determine, in a human-induced manner, whether or not an infection preventive countermeasure is required with respect to each patient, so that when an examination is to be carried out on a patient who requires disinfection, the medical image diagnosis apparatus and the examination room are manually disinfected. For this reason, there is a possibility that human-induced errors may occur, and also, a large workload is imposed on the medical staff.

BRIEF DESCRIPTION OF THE DRAWINGS

FIG. 2 is a block diagram illustrating exemplary configurations of the disinfection management device and an X-ray computed tomography apparatus according to the embodiment; and FIG. 3 is a flowchart illustrating a flow in a disinfection controlling process performed by the disinfection management device.

DETAILED DESCRIPTION

Figure 1:
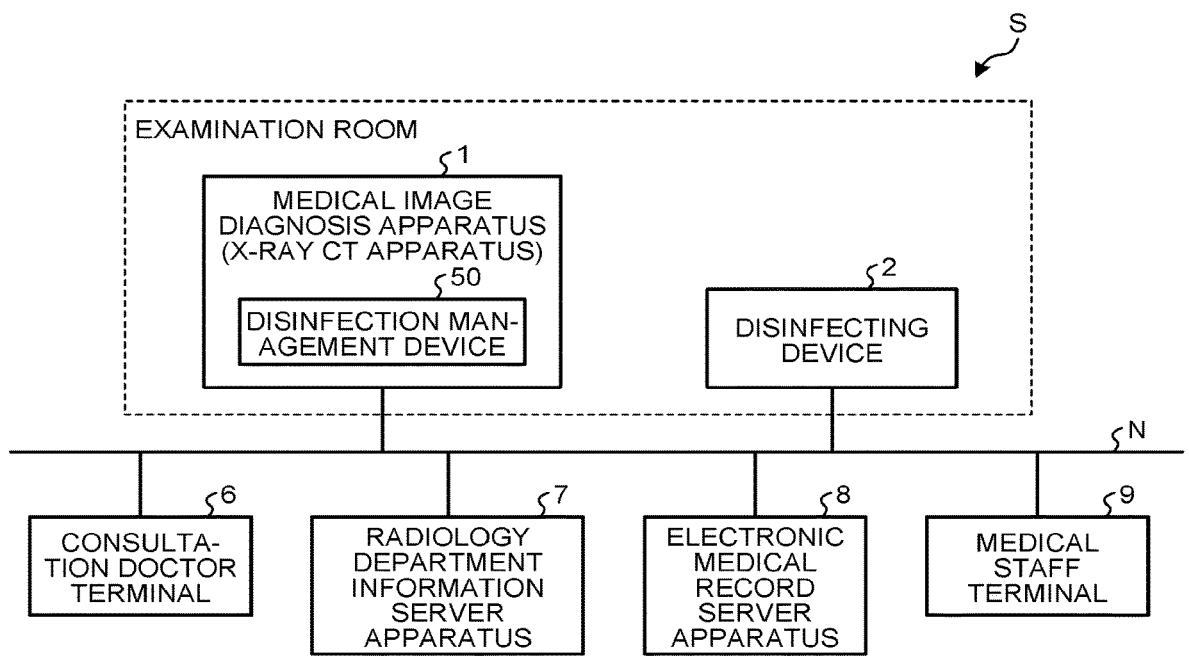
FIG. 1 is a diagram illustrating a hospital information processing system including a disinfection management device and a medical image diagnosis apparatus according to an embodiment.

A medical image diagnosis apparatus according to an embodiment is installed in an examination room and includes an obtaining unit, a judging unit, and an output unit. The obtaining unit is configured to obtain patient information about a patient undergoing an image diagnosing process that uses the medical image diagnosis apparatus. The judging unit is configured to determine specifics of control related to disinfection, on the basis of the patient information. The output unit is configured to output the determined specifics of the control.

A disinfection management device and a medical image diagnosis apparatus according to an embodiment of the present disclosure will be explained below, with reference to the accompanying drawings. To explain a specific situation, an example will be explained in which the medical image diagnosis apparatus serving as an apparatus according to the present embodiment is an X-ray Computed Tomography apparatus (hereinafter "X-ray CT apparatus"). In the present embodiment the term "disinfection" refers to treatment for the purpose of decreasing the amount of bacteria, bacterial spores, and/or virus. Typical examples of disinfection include, but are not limited to, coating or applying or spraying or dispersing appropriate medical agent (medicament). Disinfection may also be treatment for decreasing the amount of targeted bacteria, bacterial spores, and/or virus by applying physical energy such as ultraviolet irradation, for example. Further, in the embodiments described below, some of the constituent elements that are referred to by using mutually the same reference characters are assumed to perform mutually the same operations, and duplicate explanations thereof will be omitted as appropriate.

FIG. 1 is a diagram illustrating a medical information processing system S including: an X-ray CT apparatus 1 that has a disinfection management device 50 built therein, a disinfection device 2, a consultation doctor terminal 6, a radiology department information server apparatus 7, an electronic medical record server apparatus 8, and a medical staff terminal 9.

The devices and the apparatuses included in the medical information processing system S are capable of communicating with one another via a network N. In this situation, the network N may be any of the following: a wired communication network, a wireless communication network, and a network in which both wired and wireless communication are carried out.

The X-ray CT apparatus 1 and the disinfection device 2 are installed in an examination room of a hospital, for example. In this situation, the examination room is a space (a room) in which examinations using the X-ray CT apparatus 1 are carried out and may be called an imaging room. The consultation doctor terminal 6 is installed in a space (typically a diagnosis room) in which a consultation doctor provides medical consultations for patients. The radiology department information server apparatus 7 and the electronic medical record server apparatus 8 are typically installed in the hospital. The medical staff terminal 9 is installed, for example, at a reception desk, a nurse center, or the like of the hospital. Alternatively, for example, the radiology department information server apparatus 7 and the electronic medical record server apparatus 8 may be installed outside the hospital, as long as the environment allows these apparatuses to communicate with the other apparatuses and devices included in the medical information processing system S via the network N.

On the basis of examination order information from the radiology department information server apparatus 7, the X-ray CT apparatus 1 is configured to perform an imaging process on a patient (or an examined subject) in response to an operation performed by a technologist or the like. As a result of performing the imaging process, the X-ray CT apparatus 1 is configured to acquire projection data related to the patient. On the basis of the projection data, the X-ray CT apparatus 1 is configured to generate reconstructed image serving as a medical image and to transmit the generated medical image together with the examination order information to a server apparatus in a medical image management system (which is not illustrated and may be referred to as a Picture Archiving and Communication System [PACS]).

The disinfection management device 50 is configured to manage disinfection of the X-ray CT apparatus 1 and the examination room in which the X-ray CT apparatus 1 is installed. Further, the disinfection management device 50 is configured to control the disinfection device 2 when disinfection is carried out for the examination room in which the X-ray CT apparatus 1 is installed. In this situation, the disinfection for the examination room includes one or both of: disinfection of the X-ray CT apparatus 1; and disinfection of the examination room in which the X-ray CT apparatus 1 is installed. Further, the disinfection of the examination room in which the X-ray CT apparatus 1 is installed includes at least one of the following: disinfecting the air in the examination room; disinfecting the walls and the ceiling of the examination room and various types of apparatuses, devices, and equipment provided in the examination room; disinfecting traveling paths (so-called lines of flow) in the examination room; and disinfecting traveling paths to the examination room.

More specifically, the disinfection management device 50 is configured to determine whether or not the disinfection for the examination room is necessary, on the basis of information obtained from the radiology department information server apparatus 7 and the electronic medical record server apparatus 8, or the like. Upon determination that the disinfection for the examination room is necessary, the disinfection management device 50 is configured to control the disinfection device 2 when the disinfection for the examination room is carried out, as being triggered by the end of an examination (i.e., when the examination is finished) or the like. Configurations and operations of the disinfection management device 50 and the X-ray CT apparatus 1 will be explained in detail later.

The disinfection device 2 is configured to carry out the disinfection for the examination room, according to the control exercised by the disinfection management device 50. For example, the disinfection device 2 may be a disinfectant spray device or the like installed on the ceiling and/or one or more walls of the examination room. In this situation, the disinfection device 2 may be of any type, as long as the device is configured to carry out the disinfection for the examination room under the control of the disinfection management device 50. For example, the disinfection device 2 may be of a self-propelled type or a robot-type or may be built in or installed with the X-ray CT apparatus 1.

The consultation doctor terminal 6 is a computer installed in a diagnosis/treatment room, for example and is configured to generate the examination order information related to the examination performed on the patient by using the X-ray CT apparatus 1, according to an input operation of the consultation doctor. For example, the consultation doctor terminal 6 is configured to generate information related to whether or not disinfection for the examination room is necessary (hereinafter, "disinfection necessity information") according to an input operation of the consultation doctor. The consultation doctor terminal 6 is configured to transmit the generated examination order information to the radiology department information server apparatus 7 via the network N.

In this situation, in addition to information identifying the patient (patient ID information) and examination appointment information (examination time and date, etc.), the examination order information includes, for example, at least one of the following: a purpose of the examination (the type of the examination), information identifying the medical image diagnosis apparatus to be used, imaging conditions (an X-ray tube voltage and an X-ray tube current), a site to be imaged (a diagnosed site), an imaging method (whether or not a contrast agent is used, etc.), a posture of the patient during the imaging, and reconstruction conditions. Further, the disinfection necessity information includes, for example, a flag value indicating whether or not disinfection serving as an infectious disease preventive countermeasure is necessary, by using "1" for "necessary" and "0" for "not necessary"; and information designating, when the disinfection is necessary, the timing to carry out the disinfection such as "carry out before the examination" or "carry out after the examination". The disinfection necessity information may be included in the examination order information.

The consultation doctor terminal 6 may be a mobile terminal (a notebook computer, a tablet computer, or the like).

The radiology department information server apparatus 7 is a computer apparatus configured to perform processes related to information management of a radiology department information system (which may be called a Radiology Information System [RIS]). In this situation, the RIS is an information system configured to manage information in the radiology department of the hospital. Further, the radiology department information server apparatus 7 may be referred to as an RIS server.

The radiology department information server apparatus 7 is, for example, configured to receive the examination order information from the consultation doctor terminal 6 via the network N. The radiology department information server apparatus 7 is configured to transmit the examination order information to the X-ray CT apparatus 1 specified by the examination order information. In addition, when transmitting the examination order information to the X-ray CT apparatus 1, the radiology department information server apparatus 7 may append the patient ID information and the examination appointment information to a Digital Imaging and Communication in Medicine (DICOM) tag or the like.

The electronic medical record server apparatus 8 is a computer apparatus configured to perform processes related to information management of an electronic medical record system. In this situation, the electronic medical record system is an information system configured to manage electronic medical records for recording details of diagnosis/treatment processes and is a part of a Hospital Information System (HIS). The electronic medical record server apparatus 8 may simply be referred to as an electronic medical record server.

In addition to information identifying each patient (patient ID information) and additional information (name, gender, height, weight, etc.) related to the patient, for example, an electronic medical record includes at least one of the following: information related to health conditions of the patient, information related to symptoms, information related to examinations (e.g., an examination history, examination results), information related to diagnoses (e.g., a diagnosis history, diagnosis results), information related to prescribed medications (e.g., past prescribed medications, present prescribed medications, etc.), information related to a medical history, information related to a treatment history, and information related to circumstances. Further, the information related to circumstances indicate, for example, the circumstance in which the patient was injured such as "a traffic accident; admitted via emergency transport" or "injured while working at an outdoor construction site".

The electronic medical record server apparatus 8 is configured to manage the electronic medical record for each patient. For example, the electronic medical record server apparatus 8 is configured to record therein information entered in the electronic medical record of the patient through the consultation doctor terminal 6. Further, in response to a request from the disinfection management device 50, the electronic medical record server apparatus 8 is configured to transmit the electronic medical record (or at least part of the information included in the electronic medical record) of the patient to the disinfection management device 50.

The medical staff terminal 9 may be a computer provided at a reception desk, a nurse center, or the like of the hospital; a mobile terminal (e.g., a notebook computer or a tablet computer) carried around by medical staff; or the like. The medical staff terminal 9 is configured to generate additional information related to the patient, according to input operations performed by the medical staff such as a receptionist, a nurse, or the like. In this situation, the additional information related to the patient is information for specifying a specific symptom and a patient, such as "Patient A: fever and cough", "Patient B: difficulty in breathing". When there is an infection preventive countermeasure protocol in a facility such as the hospital, the additional information related to the patient is, for example, entered as appropriate by the medical staff through the medical staff terminal 9 in accordance with a management level for infectious disease prevention. Via the network N, the medical staff terminal 9 is configured to transmit the generated additional information related to the patient, to the electronic medical record server apparatus 8, for example. The electronic medical record server apparatus 8 is configured to manage the received additional information related to the patient as information included in the electronic medical record. In the present embodiment, an example will be explained in which the additional information related to each patient is managed as information included in an electronic medical record. Alternatively, it is also possible to manage the additional information related to each patient as information included in the examination order information or as stand-alone information.

Next, configurations of the disinfection management device 50 and the X-ray CT apparatus 1 having the disinfection management device 50 built therein will be explained in detail. FIG. 2 is a block diagram illustrating exemplary configurations of the disinfection management device 50 and the X-ray CT apparatus 1 having the disinfection management device 50 built therein. As illustrated in FIG. 2, the X-ray CT apparatus 1 includes a gantry 10, a table 30, and a console 40.

In the present embodiment, the rotation axis of a rotating frame 13 in a non-tilted state or the longitudinal direction of a tabletop 33 of the table 30 is defined as a Z-axis direction. An axis direction orthogonal to the Z-axis direction and parallel to the floor surface is defined as an X-axis direction. An axial direction orthogonal to the Z-axis direction and perpendicular to the floor surface is defined as a Y-axis direction.

The gantry 10 includes an imaging system for imaging medical images used in diagnosis processes. In other words, the gantry 10 is a device including the imaging system configured to radiate X-rays onto a patient P and to acquire projection data from detection data of X-rays that have passed through the patient P. The gantry 10 includes an X-ray tube 11, a wedge 16, a collimator 17, an X-ray detector 12, an X-ray high-voltage device 14, a Data Acquisition System (DAS) 18, the rotating frame 13, a controller 15, a slip ring 19 and the table 30.

The X-ray tube 11 is a vacuum tube in which thermo electrons are emitted from a negative pole (a filament) toward a positive pole (a target), as a result of application of high voltage from the X-ray high-voltage device 14.

The wedge 16 is a filter used for adjusting an X-ray dose of the X-rays radiated from the X-ray tube 11. More specifically, the wedge 16 is a filter configured to pass and attenuate the X-rays radiated from the X-ray tube 11, so that the X-rays radiated from the X-ray tube 11 onto the patient P has a predetermined distribution.

For example, the wedge 16 may be a wedge filter or a bow-tie filter and is a filter obtained by processing aluminum so as to have a predetermined target angle and a predetermined thickness.

The collimator 17 is structured with lead plates or the like used for narrowing down a radiation range of the X-rays that have passed through the wedge 16 and is configured to form a slit with a combination of the plurality of lead plates or the like.

The X-ray detector 12 is configured to detect the X-rays that were radiated from the X-ray tube 11 and have passed through the patient P and to output an electrical signal corresponding to the amount of the X-rays to the data acquiring device (the DAS 18). For example, the X-ray detector 12 includes a plurality of rows of X-ray detecting elements in each of which a plurality of X-ray detecting elements are arranged in a channel direction along an arc centered on a focal point of the X-ray tube 11. For example, the X-ray detector 12 includes a plurality of rows of X-ray detecting elements in each of which a plurality of X-ray detecting elements are arranged in a channel direction along an arc centered on a focal point of the X-ray tube. For example, the X-ray detector 12 has a structure in which the plurality of rows of X-ray detecting elements are arranged in a slice direction (which may be called a body axis direction or a row direction), the plurality of rows each having the plurality of X-ray detecting elements arranged in the channel direction.

Further, for example, the X-ray detector 12 is a detector of an indirect conversion type including a grid, a scintillator array, and an optical sensor array. The scintillator array includes a plurality of scintillators each including a scintillator crystal that outputs light in a photon quantity corresponding to an X-ray amount becoming incident thereto. The grid is arranged on a surface of the scintillator array that is positioned on the X-ray incident side and includes an X-ray blocking plate having a function of absorbing scattered X-rays. The optical sensor array has a function of converting the light amounts from the scintillators into corresponding electrical signals and includes optical sensors configured with Photomultiplier Tubes (PMTs), for example. Alternatively, the X-ray detector 12 may be a detector of a direct conversion type that includes a semiconductor element configured to convert X-rays becoming incident thereto into an electrical signal.

The X-ray high-voltage device 14 includes: a high-voltage generating device including electrical circuits such as a transformer, a rectifier, and the like and having a function of generating the high voltage to be applied to the X-ray tube 11; and an X-ray controller configured to control the output voltage in accordance with the X-rays radiated by the X-ray tube 11. The high-voltage generating device may be of a transformer type or of an inverter type. Further, the X-ray high-voltage device 14 may be provided on the rotating frame 13 or may be provided so as to belong to a fixed frame (not illustrated) of the gantry 10. The fixed frame is a frame configured to rotatably support the rotating frame 13.

The DAS 18 includes an amplifier configured to perform an amplifying process on the electrical signals output from the X-ray detecting elements of the X-ray detector 12 and an Analog/Digital (A/D) converter configured to convert the electrical signals into digital signals. The DAS 18 is configured to generate the detection data. The detection data generated by the DAS 18 is transferred to the console 40.

The rotating frame 13 is an annular frame configured to support the X-ray tube 11 and the X-ray detector 12 so as to oppose each other and configured to rotate the X-ray tube 11 and the X-ray detector 12 via the controller 15. In addition to supporting the X-ray tube 11 and the X-ray detector 12, the rotating frame 13 may further support the X-ray high-voltage device 14 and/or the DAS 18. Further, the detection data generated by the DAS 18 is, in an example, transmitted from a transmitter including a light emitting diode and being provided on the rotating frame 13, to a receiver including a photodiode and being provided in a non-rotation part (e.g., the fixed frame) of the gantry 10, through optical communication, and is further transferred to the console 40. The method for transmitting the detection data from the rotating frame 13 to the non-rotation part of the gantry 10 is not limited to optical communication and may be realized with a data transfer method using any other contactless scheme.

The controller 15 includes: a processing circuit having a Central Processing Unit (CPU) or the like; and a driving mechanism configured with a motor, an actuator, and/or the like. Upon receipt of an input signal from an input interface circuit 43 attached to the console 40 or from an input interface attached to the gantry 10, the controller 15 has a function of controlling operations of the gantry 10 and the table 30. Further, upon receipt of input signals, the controller 15 is configured to exercise control so as to rotate the rotating frame 13 and to bring the gantry 10 and the table 30 into operation.

For example, the controller 15 is configured to tilt the gantry 10, as a result of the controller 15 rotating the rotating frame 13 on an axis parallel to the X-axis direction, on the basis of tilting angle (tilt angle) information input thereto by the input interface attached to the gantry 10. The controller 15 or an operation controlling function 45*a* included in the processing circuit 45 is an example of a controlling unit.

The table 30 is a device on which the patient P to be scanned is placed and which is configured to move the patient P. The table 30 includes a base 31, a table driving device 32, the tabletop 33, and a supporting frame 34. The base 31 is a casing configured to support the supporting frame 34 so as to be movable in the vertical directions. The table driving device 32 is a motor or an actuator configured to move the tabletop 33 on which the patient P is placed, along the long axis directions thereof (the Z-axis directions in FIG. 2). The tabletop 33 provided on the top face of the supporting frame 34 is a board on which the patient P is placed. In addition to the tabletop 33, the table driving device 32 may also move the supporting frame 34 along the long axis directions of the tabletop 33.

The table driving device 32 is configured to move the base 31 in up-and-down directions, according to control signals from the controller 15. The table driving device 32 is configured to move the tabletop 33 in the long axis directions according to control signals from the controller 15.

The console 40 is a device configured to receive operations performed on the X-ray CT apparatus 1 by a user and to reconstruct X-ray CT image data from the X-ray detection data acquired by the gantry 10. The console 40 includes a memory 41, a display 42, the input interface circuit 43, and the processing circuit 45.

The disinfection management device 50 according to the present embodiment is realized by the processing circuit 45 and the memory 41.

The memory 41 is realized by using, for example, a semiconductor memory element such as a Random Access Memory (RAM) or a flash memory, or a hard disk, an optical disk, or the like. For example, the memory 41 is configured to store therein the projection data and reconstructed image data. The memory 41 is an example of a storage unit.

In addition, the memory 41 has stored therein one or more dedicated programs for realizing the operation controlling function 45*a*, a pre-processing function 45*b*, a reconstruction processing function 45*c*, an obtaining function 45*d*, a determining function 45*e*, an output controlling function 45*f*, and a disinfection controlling function 45*g* that are explained later. The memory 41 has stored therein a table defining feature values of specific words and word collocations and the reference number of times of each of the words and the word collocations, as well as a table keeping specific text information, examinations, prescriptions, medical histories, treatments, and increased susceptibilities to infections in correspondence with one another.

The display 42 is a monitor referenced by the user and is configured to display various types of information. For example, the display 42 is configured to output medical images (CT images) generated by the processing circuit 45, a Graphical User Interface (GUI) used for receiving various types of operations from the user, and the like. For example, the display 42 is a liquid crystal display device or a Cathode Ray Tube (CRT) display device.

The input interface circuit 43 is configured to receive various types of input operations from the user, to convert the received input operations into electrical signals, and to output the electrical signals to the processing circuit 45. For example, the input interface circuit 43 is configured to receive, from the user, an acquisition condition used at the time of acquiring the projection data, a reconstruction condition used at the time of reconstructing a CT image, an image processing condition used at the time of generating a post-processing image from the CT image, and the like. Further, for example, the input interface circuit 43 is realized by using a mouse, a keyboard, a trackball, a switch, a button, a joystick, and/or the like.

The processing circuit 45 is configured to control operations of the entirety of the X-ray CT apparatus 1. For example, the processing circuit 45 includes the operation controlling function 45*a*, the pre-processing function 45*b*, the reconstruction processing function 45*c*, the obtaining function 45*d*, the determining function 45*e*, the output controlling function 45*f*, and the disinfection controlling function 45*g*. In the embodiment, processing functions executed by the constituent elements, namely, the operation controlling function 45*a*, the pre-processing function 45*b*, the reconstruction processing function 45*c*, the obtaining function 45*d*, the determining function 45*e*, the output controlling function 45*f*, and the disinfection controlling function 45*g*, are stored in the memory 41 in the form of computer-executable programs. The processing circuit 45 is a processor configured to realize the functions corresponding to the programs by reading and executing the programs from the memory 41. In other words, the processing circuit 45 that has read the programs has the functions illustrated within the processing circuit 45 in FIG. 2.

With reference to FIG. 2, the example was explained in which the single processing circuit (i.e., the processing circuit 45) realizes the processing functions executed by the obtaining function 45*d*, the determining function 45*e*, the output controlling function 45*f*, and the disinfection controlling function 45*g*. However, it is also acceptable to structure the processing circuit 45 by combining together a plurality of independent processors, so that the functions are realized as a result of the processors executing the programs.

In other words, each of the abovementioned functions may be structured as a program, so that a single processing circuit executes the programs. Alternatively, one or more specific functions may be installed in a dedicated and independent program executing circuit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41. Further, instead of saving the programs in the memory 41, it is also acceptable to directly incorporate the programs into the circuits of the processors. In that situation, the processors realize the functions by reading and executing the programs incorporated in the circuits thereof.

By employing the operation controlling function 45a, the processing circuit 45 is configured to control various types of functions of the processing circuit 45, on the basis of input operations received from the user via the input interface circuit 43. For example, via the input interface circuit 43, the operation controlling function 45a is configured to receive inputs of user information (e.g., a user ID) for a log-in purpose, examined subject information, an image taking protocol, and the like. Further, by employing the operation controlling function 45a, the processing circuit 45 is configured to exercise control related to a position determining imaging process, a main imaging process, and the like.

By employing the pre-processing function 45b, the processing circuit 45 is configured to generate data obtained by performing pre-processing processes such as a logarithmic conversion process, an offset process, an inter-channel sensitivity correcting process, a beam hardening correction, and/or the like on the detection data output from the DAS 18. The data (the detection data) before the pre-processing processes and the data after the pre-processing processes may collectively be referred to as projection data.

By employing the reconstruction processing function 45c, the processing circuit 45 is configured to generate the CT image data by performing a reconstructing process using a filtered back-projection method, a successive approximation reconstruction method, and/or the like on the projection data generated by the pre-processing function 45b under the reconstruction condition.

Further, by employing the reconstruction processing function 45c, the processing circuit 45 is configured to convert the CT image data resulting from the reconstruction into tomographic image data on an arbitrary cross-sectional plane or three-dimensional image data by using a publicly-known method, on the basis of an input operation received from the user via the input interface circuit 43.

By employing the obtaining function 45d, the processing circuit 45 is configured to obtain examination information from the radiology department information server apparatus 7 and the electronic medical record server apparatus 8, via the network N.

In this situation, patient information contains information included in at least one of: the examination order information related to the patient that is obtained from the radiology department information server apparatus 7; and the electronic medical record related to the patient that is obtained from the electronic medical record server apparatus 8.

By employing the determining function 45e, the processing circuit 45 is configured to determine whether or not disinfection for the examination room is necessary (hereinafter, "disinfection necessity judging process"), on the basis of the patient information.

In this situation, examples of the disinfection of which necessity is determined by the disinfection necessity judging process include "pre-examination disinfection" and "post-examination disinfection". The pre-examination disinfection is, for example, disinfection carried out before an examination of a patient from a viewpoint of preventing the patient from being infected, when the patient who is about to undergo the examination is determined to have low immunity. In contrast, the post-examination disinfection is disinfection carried out after an examination of a patient, from a viewpoint of preventing the next patient, a doctor, and the like involved in the subsequent examination from being infected, when the patient who has undergone the examination is infected or suspected of being infected with an infectious disease or the patient who has undergone the examination had been injured in an unsanitary condition (a situation in poor hygiene), such as in a traffic accident or at an outdoor construction site.

Next, specific examples of the disinfection necessity judging process performed by the determining function 45e included in the processing circuit 45 will be explained. It is possible to carry out any of the specific examples in an arbitrary combination.

A first specific example of the disinfection necessity judging process:

In the first specific example, the disinfection necessity judging process is carries out on the basis of the disinfection necessity information and the examined site or the like included in the examination order information related to the patient that was obtained from the radiology department information server apparatus 7.

The obtaining function 45d obtains the disinfection necessity information included in the examination order information serving as the patient information.

When the disinfection necessity information included in the examination order information serving as the patient information contains the flag "1" indicating that the disinfection is necessary, the determining function 45e determines that the disinfection is necessary with respect to the patient corresponding to the received examination order information.

On the contrary, when the disinfection necessity information included in the examination order information contains the flag "0" indicating that the disinfection is not necessary, the determining function 45e determines that the disinfection is not necessary with respect to the patient corresponding to the received examination order information.

Further, on the basis of the examined site or the like included in the examination order information, the determining function 45e determines that the disinfection is necessary with respect to the patient corresponding to the received examination order information. For example, let us discuss a situation in which the examination order information includes information such as "Purpose of Examination: To check for pneumonia caused by a new coronavirus", "Examined Site: Chest", and "Posture: Supine". In this situation, on the basis of the content of the examination order information, it is highly probable that the examination is an examination for infectious diseases of the patient. Accordingly, the determining function 45e determines that the disinfection is necessary with respect to the patient corresponding to the received examination order information. Let us discuss another situation in which, for example, the examination order information includes information such as "Purpose of Examination: To observe a bone fracture/dislocation and the shapes of joints" and "Examined Site: Thighs". In this situation, on the basis of the content of the examination order information, the probability of the examination being an examination for infectious diseases of the patient is low. Accordingly, the determining function 45e determines that the disinfection is not necessary with respect to the patient corresponding to the received examination order information.

A second specific example of the disinfection necessity judging process:

In the second specific example, the disinfection necessity judging process is carried out on the basis of at least one of the following included in the electronic medical record related to the patient that is obtained from the electronic medical record server apparatus 8: information related to health conditions, information related to symptoms, information related to examinations; and information related to diagnoses.

The obtaining function 45d obtains at least one of the information related to health conditions, the information related to symptoms, the information related to examinations, and the information related to diagnoses, which are related to the patient and are included in electronic medical record information serving as the patient information. In the present example, let us discuss a situation in which the electronic record obtained by the obtaining function 45d includes, as the information related to health conditions, the information related to symptoms, and the information related to examinations, for example, text information reading "Symptoms include fever, cough, and expectoration; Suspected of being infected with the new coronavirus; Suspected of having pneumonia; PCR test; CT examination on the chest".

In this situation, from the text information included in the electronic medical record, the determining function 45e calculates, as a feature value, the number of times of appearance of each of the words (tokens) such as "fever", "cough", "expectoration", "corona", "virus", "infected", and "PCR test" and each collocation of words (vocabulary) including the tokens, by performing natural language processing. Further, the determining function 45e compares the feature values of the specific words and the collocations with the table defining the reference number of times for each of the words and each of the word collocations. When the feature values of specific words or word colocations are equal to or larger than the reference numbers of times, the determining function 45e determines that the patient is a patient infected or suspected of being infected with an infectious disease. On the contrary, when the feature values of the specific words or word colocations are no larger than the reference numbers of times, the determining function 45e determines that the patient is a patient infected or is not suspected of being infected with an infectious disease. Upon determination that the patient is a patient infected or suspected of being infected with an infectious disease, the determining function 45e determines that the disinfection is necessary after the examination of the patient. On the contrary, upon determination that the patient is a patient infected or not suspected of being infected with an infectious disease, the determining function 45e determines that the disinfection is not necessary after the examination of the patient.

Alternatively, the determining function 45e may determine whether or not the disinfection is necessary by using an AI model configured to carry out classification, on the basis of the information included in the electronic medical record information. For example, the determining function 45e may be configured to receive an input of the text information (words, phrases, and sentences, or the like) included in the electronic medical record, image information, or the abovementioned feature values and to output the classification indicating whether or not the patient is a patient infected or suspected of being infected with an infectious disease. In another example, the determining function 45e may be realized by using an AI model configured to receive the input of the text information included in the electronic medical record, the image information, or the abovementioned feature values and to output whether or not the disinfection is necessary.

In this situation, it is possible to realize the AI model used for judging whether or not the patient is a patient infected or suspected of being infected with an infectious disease through a learning process that uses training data in which, for example, text information included in electronic medical records, image information, or feature values as described above serve as input data, whereas results indicating whether or not each pertinent patient is a patient infected or suspected of being infected with an infectious disease serve as supervisor data. Also, it is possible to realize the AI model used for outputting whether or not disinfection is necessary through a learning process that uses training data in which, for example, text information included in electronic medical records, image information, or feature values as described above serve as input data, whereas whether or not disinfection is necessary serves as supervisor data.

A third specific example of the disinfection necessity judging process:

In the third specific example, the disinfection necessity judging process is carried out on the basis of at least one of the following included in the electronic medical record related to the patient that is obtained from the electronic medical record server apparatus 8: information related to examinations; information related to prescribed medications, information related to a medical history; and information related to a treatment history.

The obtaining function 45d obtains at least one of the information related to examinations, the information related to prescribed medications; the information related to a medical history; and the information related to a treatment history that are related to the patient and included in the electronic medical record information serving as the patient information. Let us discuss a situation in which the electronic medical record obtained by the obtaining function 45d includes, as the information related to prescribed medications, the information related to a medical history, and the information related to treatment history, for example, text information such as "White Blood Cell Count: 3,670/µL", "Prescribed Medication: Prednisolone", "Medical History: Secondary immunodeficiency", and "Treatment History: Radiation therapy", for example.

A normal lower limit of white blood cell counts for adults is considered to be 4,000/µL. Thus, the "White Blood Cell Count: 3,670/µL" written in the electronic medical record, for example, is too low. Accordingly, it is considered that the patient has low immunity due to a decrease in the white blood cell count. Further, Prednisolone is a drug used for an oral steroid therapy. Prednisolone has an anti-inflammatory action and an immunosuppressive action and may increase susceptibility to infections as a side effect. Further, the secondary immunodeficiency denotes a state in which immunity is lowered due to a causative disease such as diabetes, liver dysfunction, or malnutrition. Further, the radiation therapy has a possibility of lowering white blood cell counts and lowering immunity, due to reduced production of blood cells (myelosuppression) caused by an impact of radiation on the bone marrow.

In that situation, the determining function 45e compares the text information such as "White Blood Cell Count: 3,670/µL" obtained by the obtaining function 45d, with the table keeping examinations, prescriptions, medication histories, treatment histories, and increased susceptibility to infections in correspondence with one another, so as to determine whether the patient is in a state of having increased susceptibility to infections on the basis of his/her examinations, prescriptions, medical history, and treatment history. Upon determination that the patient is in the state of having increased susceptibility to infections, the determining function 45e determines that the disinfection is necessary before the examination of the patient. On the contrary, upon determination that the patient is not in the state of having increased susceptibility to infections, the determining function 45e determines that the disinfection is not necessary before the examination of the patient.

Alternatively, the determining function 45e may determine whether or not the disinfection is necessary by using an AI model configured to carry out classification, on the basis of the information included in the electronic medical record information. For example, the determining function 45e may be configured to receive an input of the text information such as "White Blood Cell Count", "Prescribed Medications", "Medical history", and "Treatment History" included in the electronic medical record and to output the classification indicating whether or not the patient is in the state of having increased susceptibility to infections. In another example, the determining function 45e may be realized by using an AI model configured to receive the input of the text information such as "White Blood Cell Count" included in the electronic medical record and to output whether or not the disinfection is necessary.

In this situation, it is possible to realize the AI model used for judging whether or not the patient is in the state of having increased susceptibility to infections through a learning process that uses training data in which, for example, text information such as "White Blood Cell Count" included in electronic medical records serves as input data, whereas results indicating whether or not each pertinent patient is in the state of having increased susceptibility to infections serve as supervisor data. Also, it is possible to realize the AI model used for outputting whether or not the disinfection is necessary through a learning process that uses training data in which, for example, the text information such as "White Blood Cell Count" included in electronic medical records serves as input data, whereas whether or not the disinfection is necessary serves as supervisor data.

A fourth specific example of the disinfection necessity judging process:

In the fourth specific example, the disinfection necessity judging process is performed on the basis of information related to circumstances included in the electronic medical record related to the patient that is obtained from the electronic medical record server apparatus 8.

The obtaining function 45d obtains the information related to circumstances that is related to the patient and included in the electronic medical record information serving as the patient information. Let us discuss a situation in which the electronic medical record obtained by the obtaining function 45d includes, as the information related to circumstances, text information such as "a traffic accident; admitted via emergency transport" or "injured while working at an outdoor construction site".

In that situation, the determining function 45e determines an unsanitary condition of the patient, by comparing the text information such as "a traffic accident; admitted via emergency transport" obtained by the obtaining function 45d, with a table defining the level of an unsanitary condition for each of the pieces of information related to various circumstances. Upon determination that the unsanitary condition of the patient is equal to or higher than a reference value, the determining function 45e determines that the disinfection is necessary after the examination of the patient. On the contrary, upon determination that the unsanitary condition of the patient is no higher than the reference value, the determining function 45e determines that the disinfection is not necessary after the examination of the patient.

Alternatively, the determining function 45e may determine whether or not the disinfection is necessary by using an AI model, on the basis of the information related to the circumstances included in the electronic medical record information. For example, the determining function 45e may be configured to receive an input of the text information such as "a traffic accident; admitted via emergency transport" included in the electronic medical record and to output the classification indicating the level of the unsanitary condition of the patient. In another example, the determining function 45e may be realized by using an AI model configured to receive the input of the text information such as "a traffic accident; admitted via emergency transport" included in the electronic medical record and to output whether or not the disinfection is necessary.

In this situation, it is possible to realize the AI model used for determining the level of the unsanitary condition of the patient through a learning process that uses training data in which, for example, text information such as "a traffic accident; admitted via emergency transport" included in electronic medical records serves as input data, whereas the levels of unsanitary conditions of pertinent patients serve as supervisor data. Also, it is possible to realize the AI model used for outputting whether or not the disinfection is necessary through a learning process that uses training data in which, for example, the text information such as "a traffic accident; admitted via emergency transport" included in electronic medical records serves as input data, whereas whether or not the disinfection is necessary serves as supervisor data.

A fifth specific example of the disinfection necessity judging process:

In the fourth specific example, additional information related to the patient and entered by medical staff at the hospital in which the examination room is provided is obtained, so as to carry out the disinfection necessity judging process on the basis of the additional information related to the patient.

As the patient information, the obtaining function 45d obtains the additional information related to the patient that is created by using the medical staff terminal 9. For example, as the patient information, the obtaining function 45d obtains the additional information related to the patient and included in the electronic medical record, from the electronic medical record server apparatus 8.

When the additional information related to the patient that was obtained by the obtaining function 45d satisfies a current reference level for infection preventive management according to an infection preventive countermeasure protocol, the determining function 45e determines that the disinfection is necessary before the examination of the patient.

On the contrary, when the additional information related to the patient that was obtained by the obtaining function 45d does not satisfy the current reference level for infection preventive management according to the infection preventive countermeasure protocol, the determining function 45e determines that the disinfection is not necessary before the examination of the patient.

Further, by employing the determining function 45e, the processing circuit 45 determines a status of the examination using the X-ray CT apparatus 1, on the basis of examination information related to the patient and further determines timing with which pre-examination disinfection is to be started and timing with which post-examination disinfection is to be started for the examination room, on the basis of the determined result regarding the examination status. In the following sections, the process performed by the determining function 45e to determine the timing to start the pre-examination disinfection and the timing to start the post-examination disinfection will be referred to as a "disinfection timing determining process".

In this situation, the examination information is information used for determining the progress of the examination performed on the patient while using the X-ray CT apparatus 1. For example, the examination information includes at least one of: an examination protocol included in the examination order information; an operation status of the X-ray CT apparatus 1; a value measured by a weight sensor provided for the table 30 of the X-ray CT apparatus 1; operation histories of an operation unit in the gantry 10 and of the console 40 included in the X-ray CT apparatus 1; an image or the like taken by a camera provided in the examination room.

For example, upon detecting that an examination plan (a study) of the patient is completed and closed in an application realized by the operation controlling function 45a, the determining function 45e determines that the examination is finished. Upon determination that the examination is finished, the determining function 45e determines the timing so that that the post-examination disinfection is started when a prescribed time period has elapsed since the time at which the examination plan was closed, for example.

In another example, upon detecting that the patient has left the tabletop 33 on the basis of a value measured by the weight sensor provided for the table 30 included in the X-ray CT apparatus 1, the determining function 45e determines that the examination is finished when a prescribed time period has elapsed since the time of detection. Upon determination that the examination is finished, the determining function 45e determines the timing so that the post-examination disinfection is started when a prescribed time period has further elapsed since the time at which the examination is determined to have been finished, for example. In these examples, the prescribed time periods may each arbitrarily be adjusted. For example, it is possible to set a time period adjusted for each patient, by taking into consideration how long it takes for the patient to exit the examination room after leaving the table, on the basis of the age and the symptoms of the patient.

In yet another example, the determining function 45e may determine the time at which the examination is finished, by judging the positions and the postures of the patient and the medical staff in the examination room, on the basis of an image taken by a camera provided in the examination room and further estimating a progress status of the examination from the determined result. Further, it is possible to realize the determining function 45e described above, for example, by using an AI model configured to receive an input of the image taken of the patient and the medical staff in the examination room and to output a result of estimating the progress status of the examination. Further, it is possible to realize the AI model through a learning process that uses training data in which, for example, images taken of patients, medical staff and the like in the examination room serve as input data, whereas progress statuses of examinations serve as supervisor data.

In yet another example, the determining function 45e may determine the time at which the examination is finished, by judging the positions and the states of the medical image diagnosis apparatus, a contrast agent injection device, an intravenous stand, a wheelchair, and a stretcher in the examination room, on the basis of an image taken by a camera provided in the examination room and further estimating a progress status of the examination from the judgment result. Further, it is possible to realize the determining function 45e described above, for example, by using an AI model configured to receive an input of the image taken of the examination apparatus, the contrast agent injection device, and the like in the examination room and to output the result of estimating the progress status of the examination. Further, it is possible to realize the AI model through a learning process that uses training data in which, for example, images taken of medical image diagnosis apparatuses, contrast agent injection devices, and the like in the examination room serve as input data, whereas progress statuses of examinations serve as supervisor data.

Further, when carrying out the disinfection in the examination room, the determining function 45e is configured to determine a disinfection target region on the basis of the examination information. For example, on the basis of an image taken by a camera provided in the examination room as the examination information, the determining function 45e is configured to determine the disinfection target region by estimating lines of flow and contact locations of the patient and the medical staff during the examination. Further, as the examination information, on the basis of an operation history of the input interface circuit 43 of the console 40 and an operation history of the operation unit provided for the gantry 10, the determining function 45e is configured to determine the disinfection target region by estimating lines of flow and contact locations of the patient and the medical staff during the examination.

Further, on the basis of the patient information obtained by the obtaining function 45d, the determining function 45e is configured to determine conditions of the agent to be used for the disinfection (e.g., the type, the concentration level, and the spraying method of the agent, the size of the agent particles at the time of spraying). For example, on the basis of the information related to health conditions, the information related to symptoms, the information related to examinations, the information related to diagnoses, and the like that are related to the patient and included in the electronic medical record information serving as the patient information, the determining function 45e determines the type and the concentration level of the disinfectant to be used in the disinfection, so that the determined type and concentration level of the disinfectant are determined. The reason why the type and the concentration level of the disinfectant are selected on the basis of the information included in the electronic medical record information is that the type and the concentration level (e.g., a high level disinfectant, a medium level disinfectant, or a low level disinfectant) of the disinfectant that are suitable vary depending on the types of bacteria, viruses, and bacterial spores to be disinfected.

By employing the output controlling function 45f, the processing circuit 45 is configured to output a result of the disinfection necessity judging process performed by the determining function 45e. For example, when carrying out the pre-examination disinfection or the post-examination disinfection, the output controlling function 45f is configured, at a stage prior to the disinfection, to cause the display 42 of the X-ray CT apparatus 1 or a separately-provided display device to display a notification message at a time earlier, by a prescribed length of time, than the disinfection start time determined by the determining function 45e used as a reference. The notification message is an example of the information notifying that the disinfection is to be carried out and is a message such as "A disinfection operation will start in one minute" or "Disinfection will be carried out in XX seconds" with a countdown. By using the message, it is possible to notify that the disinfection operation will be carried out, so as to prompt the patient, the medical staff, and the like in the examination room to take an action such as evacuating from the examination room. In this situation, the output controlling function 45f is an example of the output unit.

Alternatively, instead of displaying the message on the display 42 or the like, the output controlling function 45f may cause a speaker to output a message using speech such as "Disinfection will start in one minute" or "Disinfection will be carried out in XX seconds" with a countdown, for example.

By employing the disinfection controlling function 45g, the processing circuit 45 is configured to exercise control related to the disinfection in the examination room. When the determining function 45e determines that the pre-examination disinfection is necessary, the disinfection controlling function 45g is configured to control the disinfection device 2 to perform a disinfecting operation, prior to the examination of the patient. In this situation, the pre-examination disinfection may be performed at any time between when the examination of the previous patient is finished and when the current patient enters the examination room. Further, when the determining function 45e determines that the post-examination disinfection is necessary, the disinfection controlling function 45g is configured to control the disinfection device 2 to perform a disinfecting operation, after the examination of the patient. In this situation, the post-examination disinfection may be performed at any time between when the examination of the current patient is finished and when the next patient enters the examination room.

For example, by using the time determined by the determining function 45e to be the end of the examination as a reference, the disinfection controlling function 45g is configured to control the disinfection device 2 so as to carry out the disinfecting operation.

Alternatively, after the output controlling function 45f outputs the notification message related to the disinfection, the disinfection controlling function 45g may carry out the pre-examination disinfection or the post-examination disinfection, as being triggered by an explicit start instruction from the user via the input interface circuit 43.

Further, the disinfection controlling function 45g is configured to control the disinfection device 2 so as to disinfect the disinfection target region determined by the determining function 45e.

Furthermore, the disinfection controlling function 45g is configured to control the disinfection device 2 so as to carry out the disinfection, according to the agent conditions to be used for the disinfection that were determined by the determining function 45e.

A Disinfection Controlling Process

Next, a disinfection controlling process performed by the disinfection management device 50 structured as described above will be explained.

FIG. 3 is a flowchart illustrating a flow in the disinfection controlling process according to the present embodiment. As a premise of the disinfection controlling process illustrated in FIG. 3, it is assumed that the consultation doctor terminal 6 has transmitted the examination order information of the patient to the radiology department information server apparatus 7 via the network N.

Via the network N, the obtaining function 45d obtains the examination order information regarding the patient from the radiology department information server apparatus 7 and the electronic medical record of the patient from the electronic medical record server apparatus 8, as the patient information (step S1).

On the basis of the obtained patient information, the determining function 45e determines whether or not disinfection for the examination room is necessary (step S2). In other words, on the basis of the obtained patient information, the determining function 45e determines whether or not pre-examination disinfection is necessary and whether or not post-examination disinfection is necessary, with respect to the patient.

In the disinfection necessity judging process, when the disinfection is determined to be necessary (step S2: "NECESSARY"), the determining function 45e determines, on the basis of the examination information, a disinfection start time, agent conditions, and a disinfection target region, with respect to the type of the disinfection (the pre-examination disinfection and/or the post-examination disinfection) determined to be necessary (step S3). On the contrary, in the disinfection necessity judging process, when the disinfection is determined to be not necessary (step S2: "NOT NECESSARY"), the process proceeds to step S11 again.

The output controlling function 45f causes the display 42 or the like to output a notification message related to a warning about the disinfection (step S4).

On the basis of the disinfection start time, the agent conditions, and the disinfection target region that were determined, the disinfection controlling function 45g controls the disinfection device 2 so as to carry out the pre-examination disinfection process (step S5). On the contrary, when it is determined at step S2 that "the pre-examination disinfection is not necessary", the processes at steps S3, S4, and S5 related to the pre-examination disinfection are skipped.

The obtaining function 45d obtains the examination information such as an image obtained by the camera provided in the examination room, the information indicating completion of the examination plan from the operation controlling function 45a of the X-ray CT apparatus 1, and/or the information from the weight sensor or the like provided for the table 30 (step S6).

On the basis of the obtained examination information, the determining function 45e determines whether or not the examination of the patient has been finished (step S7). When the determining function 45e determines that the examination of the patient has not been finished (step S7: No), the obtaining function 45d keeps obtaining the examination information. On the contrary, when the determining function 45e determines that the examination of the patient has been finished (step S7: "Yes"), the process proceeds to step S8.

On the basis of the examination information such as the image obtained by the camera provided in the examination room, the determining function 45e determines a disinfection target region of the post-examination disinfection (step S8).

The output controlling function 45f causes the display 42 or the like to output a notification message related to a warning about the disinfection (step S9).

On the basis of the disinfection start time, the agent conditions, and the disinfection target region that were determined, the disinfection controlling function 45g controls the disinfection device 2 so as to carry out the post-examination disinfection process (step S10). On the contrary, when it is determined at step S2 that "the post-examination disinfection is not necessary", the processes at steps S6 through S10, for example, are skipped.

On the basis of information from the radiology department information server apparatus 7 indicating whether or not the next examination is present, the determining function 45e determines whether or not there is a subsequent examination (step S11). In other words, when examination order information of the next patient is present (step S11: "Yes"), the determining function 45e repeatedly performs the processes from step S1 with respect to the next patient. On the contrary, when there is no examination order information for a next patient (step S11: "No"), the determining function 45e ends the disinfection controlling process.

Alternatively, as necessary, when there is no examination order information for a next patient at step S11, it is also acceptable to end the disinfection controlling process, after performing a disinfection operation once as an extra disinfection process.

As explained above, the disinfection management device 50 and the X-ray CT apparatus 1 according to the present embodiment correspond to the medical image diagnosis apparatus that is installed in the examination room and include the obtaining function 45d serving as the obtaining unit, the determining function 45e serving as the judging unit, and the output controlling function 45f serving as the output unit. The obtaining function 45d is configured to obtain the patient information about the patient undergoing the image diagnosing process using the X-ray CT apparatus 1. On the basis of the patient information, the determining function 45e is configured to determine the specifics of the control related to the disinfection for the examination room. The output controlling function 45f is configured to output the determined specifics of the control.

Consequently, the specifics of the control related to the disinfection for the examination room are automatically determined on the basis of a unified standard represented by the examination information of the patient. For this reason, with respect to the examination of the patient, there is no need to determine, in a human-induced manner, the specifics of the control related to the disinfection for the examination room. As a result, it is possible to reduce the workload imposed on the medical staff such as the doctors, the technologists, and the like, as well as the occurrence of human-induced errors in judging whether or not the infection preventive countermeasures are necessary.

Further, the determining function 45e is configured to determine whether or not the disinfection for the examination room is necessary on the basis of the patient information. The output controlling function 45f is configured to output the judgment result indicating whether or not the disinfection for the examination room is necessary.

Consequently, whether or not the disinfection for the examination room is necessary is automatically determined on the basis of a unified standard represented by the examination information of the patient. For this reason, with respect to the examination of the patient, there is no need to determine, in a human-induced manner, whether or not the infection preventive countermeasures are necessary. As a result, it is possible to reduce the workload imposed on the medical staff such as the doctors, the technologists, and the like, as well as the occurrence of human-induced errors in judging whether or not the infection preventive countermeasures are necessary.

Further, the obtaining function 45d is configured to obtain, as the patient information, at least one of the following included in the examination order information related to the image diagnosing process performed on the patient: the disinfection necessity information; the purpose of the examination; the imaged site of the image diagnosing process; the imaging conditions of the image diagnosing process; and the imaging method of the image diagnosing process. The determining function 45e may be configured to determine whether or not the disinfection for the examination room is necessary, on the basis of at least one of the disinfection necessity information, the imaged site, and the imaging conditions.

Consequently, it is possible to accurately and automatically determine whether or not the examination room used for the examination of the patient needs to be disinfected, on the basis of the information included in the examination order information created by the consultation doctor of the patient.

As the patient information, the obtaining function 42 is configured to obtain at least one of the following included in the electronic medical record of the patient: the information related to health conditions; the information related to symptoms; the information related to examinations; the information related to diagnoses; the information related to prescribed medications; the information related to the medical history; the information related to the treatment history; and the information related to the circumstances. The determining function 45e is configured to determine whether or not the disinfection for the examination room is necessary, by using: the judgment related to infectious diseases of the patient, the judgment related to increased susceptibility to infections regarding the patient, and/or the judgment related to unsanitary conditions of the patient.

Consequently, on the basis of the information included in the electronic medical record of the patient, it is automatically determined, for example, whether or not the patient is a patient infected or suspected of being infected with an infectious disease and whether or not the patient is in the state of having increased susceptibility to infections. According to these determined results, it is possible to accurately and automatically determine whether or not the disinfection for the examination room is necessary.

As the patient information, the obtaining function 45d is configured to obtain the additional information related to the patient and entered by the medical staff at the hospital in which the examination room is provided. The determining function 45e is configured to determine whether or not the disinfection for the examination room is necessary on the basis of the additional information related to the patient.

Consequently, on the basis of the additional information related to the patient and entered by the medical staff at the hospital, it is automatically determined whether or not, for example, the patient is a patient infected or suspected of being infected with an infectious disease. It is therefore possible to accurately and automatically determine whether or not the disinfection for the examination room is necessary according to the judgment result.

The obtaining function 45d is configured to obtain the information related to the management level of the hospital in which the examination room is provided. The determining function 45e is configured to determine whether or not the disinfection for the examination room is necessary on the basis of the management level.

Consequently, it is possible to accurately and automatically determine whether or not the disinfection for the examination room is necessary, on the basis of the information related to the management level of the hospital, in addition to the patient information of the patient.

Also, further provided is the disinfection controlling function 45g serving as a controlling unit configured to carry out the disinfection for the examination room by using the disinfection device 2, on the basis of the judgment result as to whether or not the disinfection for the examination room is necessary.

Consequently, when the disinfection for the examination room is determined to be necessary on the basis of the patient information, it is possible to automatically carry out the disinfection for the examination room. As a result, because there is no need to carry out the disinfecting work in a human-induced manner, it is possible to reduce the workload of the medical staff, as well as risks of infections and the like during the disinfecting work.

The determining function 45e is configured to determine the end of the examination related to the patient on the basis of the examination information related to the patient. The disinfection controlling function 45g is configured to carry out the disinfection for the examination room by using the disinfection device 2 with reference to the end of the examination related to the patient determined by the determining function 45e.

Consequently, when the disinfection for the examination room is determined to be necessary on the basis of the patient information, it is possible to determine the end of the examination on the basis of the examination information related to the patient and to further carry out the disinfection for the examination room by using the disinfection device 2 on the basis of the determined result. Accordingly, because it is possible to carry out the disinfection with the timing suitable for the examination room, there is no need to check to see whether cleaning can be carried out or to perform an operation to cause the cleaning process to be performed, before and after the end of the examination, for example. As a result, it is possible to improve efficiency of the disinfecting work.

As the examination information, the obtaining function 45d is configured to obtain at least one of the following: the examination protocol included in the examination order information; an operation status of the X-ray CT apparatus 1; the value measured by the weight sensor provided for the table 30 included in the X-ray CT apparatus 1; an operation history of the X-ray CT apparatus 1; and an image taken by the camera provided in the examination room.

Consequently, when the disinfection for the examination room is determined to be necessary on the basis of the patient information, it is possible to more accurately determine the time at which the examination was finished, on the basis of the examination protocol included in the examination order information or the like.

The determining function 45e is configured to determine the disinfection target region of the examination room on the basis of the examination information related to the patient. The disinfection controlling function 45g is configured to carry out the disinfection on the disinfection target region, by using the disinfection device 2.

Consequently, when the disinfection for the examination room is determined to be necessary on the basis of the patient information, it is possible to automatically carry out the disinfection with reference to regions touched by the patient, the lines of flow, and the like as the disinfection target region. As a result, it is possible to accurately disinfect the regions that need to be disinfected with respect to the examination room. It is therefore possible to improve efficiency of the disinfecting work and to reduce risks of infections and the like.

The determining function 45e is configured to determine the agent conditions to be used for the disinfection, on the basis of the patient information. The disinfection controlling function 45g is configured to carry out the disinfection for the examination room by using the disinfection device 2 according to the agent conditions.

Consequently, when the disinfection for the examination room is determined to be necessary on the basis of the patient information, it is possible to automatically determine the agent conditions to be used for the disinfection, in accordance with which infectious disease is concerned or the like, on the basis of the patient information. As a result, it is possible to carry out the disinfection by using a type of agent and a concentration level suitable for the examination room. It is therefore possible to improve efficiency of the disinfecting work and to also reduce risks of infections and the like.

The output controlling function 45f is configured to output the information notifying that the disinfection for the examination room is to be carried out.

Consequently, the patient and the medical staff are able to understand the disinfection start time, from the notification message displayed on a monitor or the audio, for example. As a result, it is possible to take an action such as exiting the examination room, before the disinfection is started. It is therefore possible to improve efficiency of the disinfecting work.

FIRST MODIFICATION EXAMPLE

In the embodiment above, the example was explained in which the disinfection for the examination room in which the X-ray CT apparatus 1 is installed is managed. In addition, it is also possible to apply the present disclosure to a situation where, for example, disinfection is managed with respect to a space used by a patient infected with an infectious disease, such as a diagnosis room, a treatment room, a waiting room, a passage, or the like. It is possible to realize the management in this situation, for example, by having the disinfection management device 50 built in a computer provided in the diagnosis room, the treatment room, or the like. Further, it is also acceptable to configure the disinfection management device 50 so as to perform the disinfection necessity judging process and to output a judgment result, so that the disinfection process itself is performed with separate timing.

SECOND MODIFICATION EXAMPLE

In the embodiment above, the example was explained in which it is independently determined both whether the pre-examination disinfection is necessary and whether the post-examination disinfection is necessary, so that when the disinfection is determined to be necessary in each of the judging processes, the pre-examination disinfection and the post-examination disinfection are both carried out. Alternatively, for example, when the post-examination disinfection is determined to be necessary with respect to the examination of the current patient, and also the pre-examination disinfection is determined to be necessary with respect to the examination of the next patient, it is also acceptable to omit one of the post-examination disinfection and the pre-examination disinfection.

Further, when the disinfection necessity judging process for the examination room is omitted, as described in the third modification example below, the process at step S2 in FIG. 3 will be omitted. Further, it is also acceptable to omit, as appropriate, outputting the disinfection warning at steps S4 and S9 in FIG. 3.

THIRD MODIFICATION EXAMPLE

In the embodiment above, the example was explained in which the obtaining function 45d is configured to obtain the patient information, while the determining function 45e is configured to determine whether or not the disinfection for the examination room is necessary on the basis of the content of the patient information. Alternatively, it is also acceptable to determine whether or not the disinfection for the examination room is necessary, on the basis of a management level for infectious disease countermeasures and the like of the entire hospital in which the examination room is provided. For example, when the management level for infectious disease countermeasures and the like of the entire hospital is at the "highest alert level", it is acceptable to omit the disinfection necessity judging process for the examination room based on the patient information (i.e., to omit the process at step S2), so that the disinfection for the examination room is carried out before or after the examinations of all the patients. In contrast, when the management level for infectious disease countermeasures and the like of the entire hospital is at an "alert level", it is acceptable to perform the disinfection necessity judging process for the examination room, on the basis of the content of the patient information.

Further, for example, when the management level for infectious disease countermeasures and the like of the entire hospital is at the "highest alert level", it is also acceptable to determine specifics of the control related to the disinfection for the examination room, on the basis of the patient information. For example, on the basis of the patient information, the determining function 45e may be configured to determine the specifics of the control related to the disinfection for the examination room such as a disinfection start time, a disinfection target region, agent conditions, and the like. In that situation, the output controlling function 45f is configured to cause the display 42 or the like to output the determined specifics of the control.

FOURTH MODIFICATION EXAMPLE

The medical image diagnosis apparatus having the disinfection management device 50 built therein according to the present embodiment is not limited to the X-ray CT apparatus 1 and may be an X-ray diagnosis apparatus, a Positron Emission Tomography (PET)-CT system, an angio-CT system, a magnetic resonance imaging apparatus, a nuclear medical diagnosis apparatus, or an ultrasound diagnosis apparatus, for example.

For instance, when the medical image diagnosis apparatus is a Magnetic Resonance Imaging (MRI) apparatus, the disinfection timing determining process may determine the status of an examination using the MRI apparatus, on the basis of a reception coil connection status. For example, the determining function 45e may be configured to monitor the reception coil connection status of the MRI apparatus and to detect when all the reception coils are removed, so as to determine that the examination is finished when a prescribed time period has elapsed since the removal detection time. Upon determination that the examination is finished, the determining function 45e may be configured to determine that post-examination disinfection is to be started when a prescribed time period has further elapsed since the time at which the examination is determined to have been finished, for example.

FIFTH MODIFICATION EXAMPLE

In the embodiment above, the example was explained in which the X-ray CT apparatus 1 includes the function serving as the disinfection management device 50. Alternatively, the disinfection management device 50 communicable with at least one of the X-ray CT apparatus 1, the consultation doctor terminal 6, the radiology department information server apparatus 7, the electronic medical record server apparatus 8, and the medical staff terminal 9 may be implemented by using a medical workstation or a personal computer, for example. Such a disinfection management device 50 may be installed not only inside the hospital, but also in a facility outside the hospital or in a computing cloud. The disinfection management device 50 is an example of a disinfection management apparatus.

SIXTH MODIFICATION EXAMPLE

The timing to perform the disinfection necessity judging process is not limited to the examples in the above embodiments. For instance, when the examination schedule for the day has been confirmed, it is also possible to collectively perform the disinfection necessity judging processes with respect to all the patients, before the first examination of the day, for example.

SEVENTH MODIFICATION EXAMPLE

The above embodiment has described the disinfection device 2 and the disinfection management device 50 as independent devices, by way of example. Alternatively, the disinfection device 2 may be configured to additionally include the functions of the disinfection management device 50. In such a case the disinfection device 2 is communicable with at least one of the X-ray CT apparatus 1, the consultation doctor terminal 6, the radiology department information server apparatus 7, the electronic medical record server apparatus 8, and the medical staff terminal 9. Moreover, such a disinfection device 2 can have various forms including floor standing or ceiling- or wall-mounted in the examination room, automated, mobile, robotic, and integrated with the medical image diagnosis apparatus, for example. The disinfection device 2 is an example of a disinfection apparatus.

According to at least one aspect of the embodiments and the modification examples described above, it is possible to reduce the occurrence of human-induced errors and to decrease the workload of the medical staff, regarding the disinfection of the medical image diagnosis apparatus, the examination room, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus to be installed in an examination room, the apparatus comprising an imaging system and processing circuitry, the processing circuitry configured to:
   obtain patient information about a patient to undergo an image diagnosing process performed by the medical image diagnosis apparatus;
   determine specifics of disinfection control for the examination room on a basis of the patient information; and
   cause an output circuit to output the determined specifics of the control,
   wherein the processing circuitry is further configured to:
   determine, as the specifics of the control, necessity or unnecessity of the disinfection in the examination room;
   cause the output circuit to output a result of the determination as to necessity or unnecessity of the disinfection in the examination room;
   obtain, as the patient information, at least one of: disinfection information indicating necessity or unnecessity of disinfection, an examination purpose, a site to be imaged for the image diagnosing process, an imaging condition for the image diagnosing process, and an imaging method used in the image diagnosing process, all of which are included in examination order information related to the image diagnosing process with respect to the patient.

2. The medical image diagnosis apparatus according to claim 1, wherein
   the processing circuitry is further configured to:
   obtain as the patient information, at least one of:
      health-condition information;
      symptom information;
      examination information;
      diagnosis information;
      prescribed-medication information;
      medical history information;
      treatment history information; and
      circumstances information, all of which are included in an electronic medical record of the patient, and
   determine necessity or unnecessity of the disinfection in the examination room on a basis of a result of determination of at least one of:
   determination as to an infectious disease of the patient;
   determination as to increased susceptibility of the patient to infections; and
   determination as to an unsanitary condition of the patient.

3. The medical image diagnosis apparatus according to claim 1, wherein the processing circuitry is further configured to:
   obtain additional information about the patient as the patient information, the additional information being entered by medical staff at a hospital including the examination room, and
   determine necessity or unnecessity of the disinfection in the examination room on a basis of the additional information about the patient.

4. The medical image diagnosis apparatus according to claim 1, wherein the processing circuitry is further configured to:
   obtain information related to a management level of the hospital including the examination room, and
   determine necessity or unnecessity of the disinfection in the examination room on a basis of the management level.

5. The medical image diagnosis apparatus according to claim 1, further comprising:
   a control circuit configured to carry out the disinfection in the examination room using a disinfection apparatus, on a basis of a result of the determination as to necessity or unnecessity of the disinfection in the examination room.

6. The medical image diagnosis apparatus according to claim 5, wherein
   the processing circuitry is further configured to determine an end of an examination of the patient on a basis of examination information about the patient, and
   the control circuit is further configured to carry out the disinfection in the examination room using the disinfection apparatus, with reference to the end of the examination of the patient.

7. The medical image diagnosis apparatus according to claim 6, wherein
   the processing circuitry is further configured to obtain, as the examination information, at least one of:
   an examination protocol included in examination order information;
   an operation status of the medical image diagnosis apparatus;
   a measurement by a weight sensor mounted in a table of the medical image diagnosis apparatus;
   an operation history of the medical image diagnosis apparatus; and
   an image captured by a camera installed in the examination room.

8. The medical image diagnosis apparatus according to claim 5, wherein
   the processing circuitry is further configured to determine an end of an examination of another patient subjected to the image diagnosis immediately before the patient, on a basis of examination information about the another patient, and
   the control circuit is further configured to carry out the disinfection in the examination room using the disinfection apparatus before examination of the patient, with reference to the end of the examination of the patient.

9. The medical image diagnosis apparatus according to claim 6, wherein
   the processing circuitry is further configured to determine a disinfection target region in the examination room on the basis of the examination information, and
   the control circuit is further configured to carry out the disinfection of the disinfection target region using the disinfection apparatus.

10. The medical image diagnosis apparatus according to claim 6, wherein
    the processing circuitry is further configured to determine a medicament condition to be used for the disinfection, on the basis of the patient information, and
    the control circuit is further configured to carry out the disinfection in the examination room using the disinfection apparatus according to the medicament condition.

11. The medical image diagnosis apparatus according to claim 1, wherein
the processing circuitry is further configured cause the output circuit to output information indicating that the disinfection of the examination room is to be carried out.

12. A disinfection management apparatus to be installed in an imaging system, the apparatus comprising processing circuitry configured to:
obtain patient information;
determine specifics of disinfection control on a basis of the patient information; and
cause an output circuit to output the determined specifics of the disinfection control,
wherein the processing circuitry is further configured to:
determine, as the specifics of the control, necessity or unnecessity of the disinfection in the examination room;
cause the output circuit to output a result of the determination as to necessity or unnecessity of the disinfection in the examination room;
obtain, as the patient information, at least one of: disinfection information indicating necessity or unnecessity of disinfection, an examination purpose, a site to be imaged for the image diagnosing process, an imaging condition for the image diagnosing process, and an imaging method used in the image diagnosing process, all of which are included in examination order information related to the image diagnosing process with respect to the patient.

13. A disinfection apparatus to be installed in an imaging system, the apparatus comprising:
processing circuitry configured to obtain patient information and determine necessity or unnecessity of the disinfection in the examination room on a basis of the patient information, and to cause an output circuit to output a result of the determination of the necessity or unnecessity the disinfection in the examination room; and
a control circuit configured to carry out the disinfection in the examination room on a basis of the determination result of the necessity or unnecessity the disinfection in the examination room,
wherein the processing circuitry is further configured to:
determine, as the specifics of the control, necessity or unnecessity of the disinfection in the examination room;
cause the output circuit to output a result of the determination as to necessity or unnecessity of the disinfection in the examination room;
obtain, as the patient information, at least one of: disinfection information indicating necessity or unnecessity of disinfection, an examination purpose, a site to be imaged for the image diagnosing process, an imaging condition for the image diagnosing process, and an imaging method used in the image diagnosing process, all of which are included in examination order information related to the image diagnosing process with respect to the patient.

14. The disinfection apparatus according to claim 13, wherein
the processing circuitry is further configured to determine an end of an examination of a patient on a basis of examination information about the patient, and
the control circuit is further configured to carry out the disinfection in the examination room using the disinfection apparatus, with reference to the end of the examination of the patient as determined.

15. The disinfection apparatus according to claim 13, wherein
the processing circuitry is further configured to determine an end of an examination of another patient subjected to an image diagnosing process immediately before the patient, on a basis of examination information about the another patient, and
the control circuit is further configured to carry out the disinfection in the examination room using the disinfection apparatus before examination of the patient, with reference to the end of the examination of the patient as determined.

* * * * *